United States Patent
Mian et al.

(10) Patent No.: US 11,361,848 B2
(45) Date of Patent: Jun. 14, 2022

(54) METHODS AND SYSTEMS FOR DETERMINING A CORRELATION BETWEEN PATIENT ACTIONS AND SYMPTOMS OF A DISEASE

(71) Applicant: Curelator, Inc., Palmer, MA (US)

(72) Inventors: Alec Mian, Palmer, MA (US); Jordi Villa i Freixa, Barcelona (ES)

(73) Assignee: Curelator, Inc., Palmer, MA (US)

( * ) Notice: Subject to any disclaimer, the term of this patent is extended or adjusted under 35 U.S.C. 154(b) by 1531 days.

(21) Appl. No.: 14/811,184

(22) PCT Filed: Jan. 30, 2014

(86) PCT No.: PCT/US2014/013894
§ 371 (c)(1),
(2) Date: Jul. 28, 2015

(87) PCT Pub. No.: WO2014/120947
PCT Pub. Date: Aug. 7, 2014

(65) Prior Publication Data
US 2016/0378945 A1    Dec. 29, 2016

Related U.S. Application Data

(60) Provisional application No. 61/860,893, filed on Jul. 31, 2013, provisional application No. 61/762,033, (Continued)

(51) Int. Cl.
*G16H 10/60* (2018.01)
*G16H 50/70* (2018.01)
(Continued)

(52) U.S. Cl.
CPC .............. *G16H 10/60* (2018.01); *G16H 50/50* (2018.01); *G16H 50/70* (2018.01); *G16Z 99/00* (2019.02)

(58) Field of Classification Search
CPC ........ G16H 50/20; G16H 50/30; G16H 10/60; G16H 40/67; G16H 50/50; G16H 20/10;
(Continued)

(56) References Cited

U.S. PATENT DOCUMENTS

2002/0055857 A1    5/2002  Mault
2002/0156654 A1*  10/2002  Roe .................... G06Q 10/10
                                                        705/3
(Continued)

OTHER PUBLICATIONS

Computational Systems Bioinformatics—Methods and Biomedical Applications, Zhou, X., et al., Jan. 2008 (Year: 2008).*
(Continued)

Primary Examiner — Joseph D Burgess
(74) Attorney, Agent, or Firm — McDonnell Boehnen Hulbert & Berghoff LLP (57) ABSTRACT

Example embodiments disclosed herein relate to methods and systems for determining whether particular actions affect or influence medical symptoms of patients. In one example, a plurality of datasets from a corresponding plurality of patients is received, where each patient has a
(Continued)

corresponding disease. An individual dataset for an individual patient may include information about at least one disease symptom of the patient and at least one action of the patient. After the datasets are received from the patients, the datasets are stored in a database. Using the datasets stored in the database, a correlation between one or more actions and one or more disease symptoms may be determined based on a statistical analysis of the actions and symptoms stored in the database. The correlation between the one or more actions and the one or more disease symptoms may also be stored in the database.

14 Claims, 8 Drawing Sheets

Related U.S. Application Data filed on Feb. 7, 2013, provisional application No. 61/759,231, filed on Jan. 31, 2013.

(51) Int. Cl.
*G16H 50/50* (2018.01)
*G16Z 99/00* (2019.01)

(58) Field of Classification Search
CPC ........ G16H 20/17; G16H 40/63; G16H 50/70; G16H 10/20; G16H 15/00; G16H 30/20; G16H 30/40; G16H 80/00; G16H 20/13; G16H 20/30; G16H 40/20; G16H 70/60; G16H 10/40; G16H 20/00; G16H 40/60; G16H 70/20; G16H 20/40; G16H 20/60; G16H 20/70; G06Q 50/22
USPC .......................................................... 705/2–3
See application file for complete search history.

(56) References Cited

U.S. PATENT DOCUMENTS

| | | | |
|---|---|---|---|
| 2003/0144829 A1 | 7/2003 | Geatz et al. | |
| 2009/0234627 A1* | 9/2009 | Yu ........................ | G16H 50/50 703/11 |
| 2010/0088264 A1* | 4/2010 | Teverovskiy ......... | G16H 50/20 706/46 |
| 2010/0318424 A1 | 12/2010 | LaValle | |
| 2011/0119212 A1* | 5/2011 | De Bruin ............... | G16H 50/70 706/12 |
| 2011/0184250 A1* | 7/2011 | Schmidt ................ | G06Q 10/00 600/300 |
| 2012/0036103 A1 | 2/2012 | Stupp et al. | |
| 2014/0279746 A1* | 9/2014 | De Bruin ............. | A61B 5/7267 706/12 |

OTHER PUBLICATIONS

Written Opinion dated Aug. 13, 2015 in application PCT/US2014/013894 (8 pages).
Search Report in PCT/US14/013894 dated Aug. 8, 2014 (3 pages).

* cited by examiner

METHODS AND SYSTEMS FOR DETERMINING A CORRELATION BETWEEN PATIENT ACTIONS AND SYMPTOMS OF A DISEASE

CROSS-REFERENCE TO RELATED APPLICATIONS

The present application is a U.S. National Phase of PCT application PCT/US14/13894, filed on Jan. 30, 2014 and currently pending. The PCT/US14/13894 application claims priority to provisional application numbers 61/759,231 filed on Jan. 31, 2013, 61/762,033 filed on Feb. 7, 2013, and 61/860,893 filed on Jul. 31, 2013. The entire contents of the PCT/US14/13894, 61/759,231, 61/762,033, and 61/860,893 applications are incorporated herein by reference.

FIELD

The present disclosure relates generally to methods and systems for determining whether particular actions (eating certain foods, taking specific medications, or engaging in particular exercises or other activities, for example) affect or influence medical symptoms of patients. More specifically, the present disclosure relates to methods and systems for determining a correlation between one or more actions of patients and one or more symptoms of a disease based on a statistical analysis of the actions and symptoms.

BACKGROUND

Predictive models have been, and are, commonly used to predict medical outcomes. Such models are based on statistical data obtained from populations of individuals that are identified as having or not having a particular medical outcome. The data regarding the populations of individuals is typically analyzed using statistical techniques such as linear regression or multiple linear regression (MLR), to predict the medical outcome. Generally, the models involve using controllable and/or easily measured variables (i.e., factors) to explain or predict the behavior of other variables (responses).

In its simplest form, a MLR specifies the linear relationship between a dependent variable (response) Y, and a set of independent predictor variables (factors) Xs, so that every value of the independent variable X is associated with a value of the dependent variable Y. For many data analysis problems, estimates of the linear relationships between these variables are adequate to describe the observed data, and to make reasonable predictions for new observations. For example, the weight of a person could be estimated as a function of the height of the person and the amount of exercise the person engages in. Using MLR, respective regression coefficients may be determined from a sample of data, measuring height and observing the amount of exercise of the subjects.

One problem with using the foregoing conventional predictive models to predict medical outcomes is that the models rely on factors that are few in number, are not significantly redundant (collinear), and have a well understood relationship to the responses. However, if any of these conditions vary (i.e., break down), these MLRs can be inefficient or inappropriate. Stated differently, if the number of factors gets too large, then the model will likely be unable to predict new data. This may be due to the fact that, though there are many factors, there may be only a few latent variables that account for most of the variation in response. Accordingly, using MLR to predict medical outcomes based on a large number of factors may not be feasible in some circumstances.

SUMMARY

This application discloses methods and systems for determining correlations between one or more actions of patients and one or more disease symptoms based on statistical analysis of datasets of patient actions and disease symptoms built from inputs received from a plurality of patients over time. In some embodiments, the method may include receiving and analyzing a single dataset pertaining to one patient. Some embodiments further consider patient characteristics and whether correlations of patient actions and disease symptoms vary according to particular patient characteristics. In this manner, the disclosed systems and methods are able to predict correlations between patient actions and disease symptoms based on data collected from a sufficient plurality of individual patients (or a sufficient amount of data pertaining to a single patient), and in turn, predict for an individual patient, whether performing a particular action is likely to improve a disease symptom for that particular patient.

Some embodiments include a method comprising receiving, at a computing device, a dataset from a patient. The dataset includes information about at least one disease symptom of the patient and at least one action of the patient. The method includes storing the dataset in a database comprising a tangible, non-transitory computer readable media. The method also includes determining a correlation between one or more actions and one or more symptoms of a disease based on a statistical analysis of the actions and symptoms described in the dataset. The method additionally includes storing in the database the correlation between the one or more actions and the one or more symptoms.

Some embodiments include receiving and storing a plurality of datasets from a corresponding plurality of patients, wherein the dataset for an individual patient includes information about at least one disease symptom and at least one action of the individual patient. Such embodiments further include determining and storing a correlation between one or more actions and one or more symptoms of the disease based on a statistical analysis of the actions and symptoms of the plurality of datasets received from the corresponding plurality of patients.

Some embodiments include a system comprising one or more processors configured to receive a dataset from a patient. The dataset includes information about at least one disease symptom of the patient and at least one action of the patient. The one or more processors are further configured to (1) store the dataset in a database comprising a tangible, non-transitory computer readable media; (2) determine a correlation between one or more actions and one or more symptoms of a disease based on a statistical analysis of the actions and symptoms of the of dataset; and (3) store in the database the correlation between the one or more actions and the one or more symptoms.

Some embodiments include a computing system configured to receive and store a plurality of datasets from a corresponding plurality of patients, wherein the dataset for an individual patient includes information about at least one disease symptom and at least one action of the individual patient. In such embodiments, the computing system is further configured to determine and store a correlation between one or more actions and one or more symptoms of the disease based on a statistical analysis of the actions and symptoms of the plurality of datasets received from the corresponding plurality of patients.

Still further embodiments include a non-transitory computer readable medium having stored therein instructions executable by a computer system to cause the computer system to perform certain functions. The functions include receiving a dataset from a patient. The dataset includes information about at least one disease symptom of the patient and at least one action of the patient. The functions include storing the dataset in a database comprising a tangible, non-transitory computer readable media. The functions also include determining a correlation between one or more actions and one or more symptoms of a disease based on a statistical analysis of the actions and symptoms of the dataset, and storing in the database the correlation between the one or more actions and the one or more symptoms.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE DRAWINGS

Preferred embodiments of the subject matter described herein will now be explained with reference to the accompanying drawings of which.

DETAILED DESCRIPTION

The following detailed description describes various features and functions of the disclosed systems and methods with reference to the accompanying figures. In the figures, similar symbols typically identify similar components, unless context dictates otherwise. The example embodiments described herein are not meant to be limiting. Other embodiments may be utilized, and other changes may be made, without departing from the scope of the subject matter presented herein. It will be readily understood that the aspects of the present disclosure, as generally described herein and illustrated in the figures can be arranged, substituted, combined, separated, and designed in a wide variety of different configurations, all of which are contemplated herein.

1. Medical Predictive Model Overview

In general, multiple linear regression (MLR) can be used to create predictive models for medical outcomes. Partial least squares regression (PLSR) extends MLRs without imposing known restrictions employed by multivariate MLR. This flexibility allows PLSR to be used in situations where the use of traditional multivariate methods may be severely limited, such as when there are fewer observations than predictor variables. Furthermore, PLSR can be used as an exploratory analysis tool to select suitable predictor variables and to identify outliers before applying classical MLR.

One feature of the methods and systems described herein is the ability to generate a predictive model for medical outcomes in the instances where the medical outcomes may be based on a plurality of variables. Another feature of the methods and systems disclosed herein is to use the generated predictive model to make recommendations to patients. More specifically, the methods and systems described herein determine a correlation between one or more actions of patients and one or more symptoms of a disease of the patients based on a statistical analysis of the actions and symptoms. Using this statistical information, recommendations may be made to the patients to undergo or take (or avoid undergoing or taking) specific actions. In certain embodiments, symptoms, actions and correlations are related interactively, wherein the effect of at least one patient's actions are evaluated with regard to the effects on patient symptoms and on the correlation between patient actions and symptoms, and wherein actions are recommended to other patients to undergo or take (or avoid undergoing or taking) that have a predicted effect on that patient's disease or symptoms.

Example embodiments disclosed herein relate to methods and systems that help determine whether particular actions (eating or avoiding certain foods, taking or avoiding specific medications, or engaging in or avoiding particular exercises or other activities, for example) affect or influence medical symptoms of patients. In one example, a plurality of datasets from a corresponding plurality of patients is received at a computing device. (In some embodiments, the method may include receiving a single dataset pertaining to one patient.) Each patient may have at least one corresponding disease. An individual dataset of each patient may include information about at least one disease symptom of the patient and at least one action of the patient. After the datasets are received from each patient, the datasets may be stored in a database. Using the datasets stored in the database, a correlation between one or more actions and one or more symptoms of the disease may be determined based on a statistical analysis of the actions and symptoms stored in the database. The correlation between the particular action and the at least one symptom may also be stored in the database.

2. Network Environment

Figure 1:
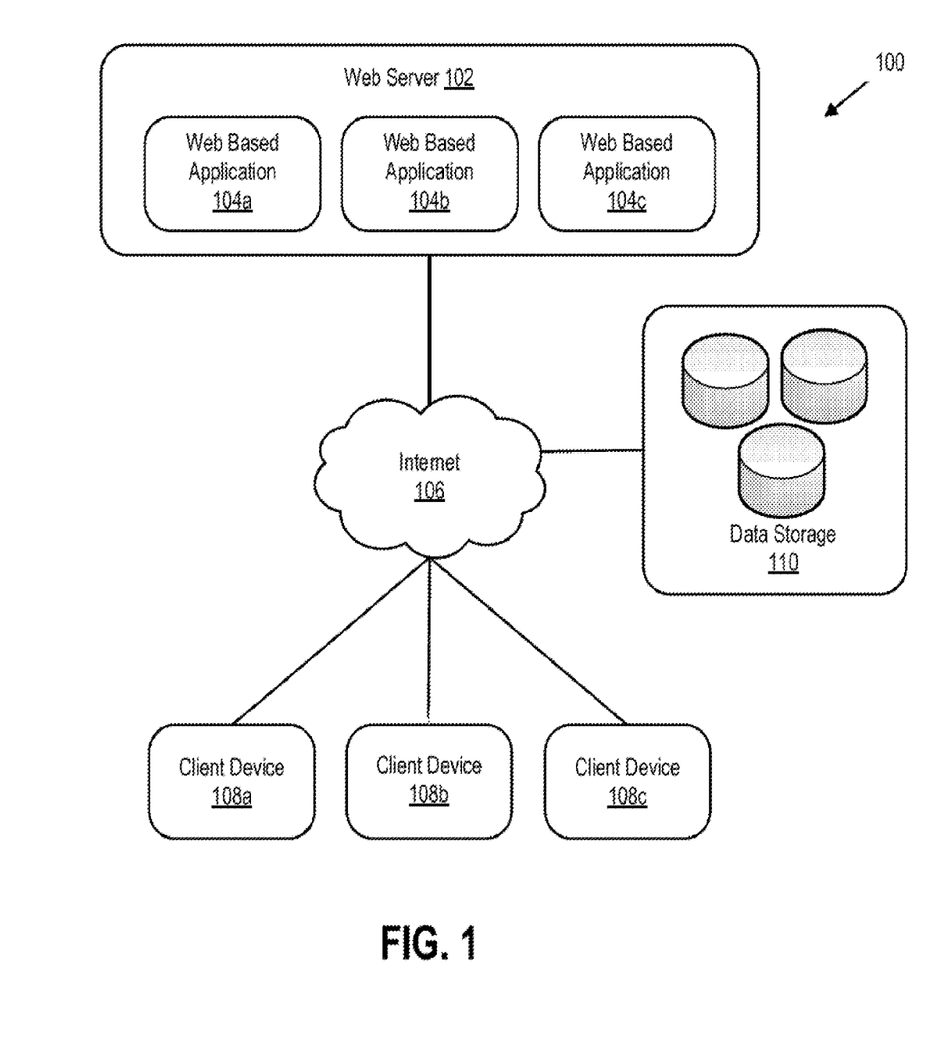
FIG. 1 illustrates a block diagram of an example system according to certain embodiments.

FIG. 1 illustrates a block diagram of one example system in which the methods disclosed herein may be implemented. The illustrated system includes a web server 102, client devices 108*a*, 108*b*, and 108*c* . . . , 108(*n*) each configured to communicate with web server 102 and data storage 110 directly or indirectly over the Internet 106.

Web server 102 may be any computing device capable of carrying out the methods and functions described herein. Web server 102 may include one or more web-based applications 104a-c that may be configured to perform the methods disclosed herein. For example, the web-based applications 104a-c may be configured to perform one or more steps of the methods discussed in reference to FIGS. 3A-3C and 4. The web applications may be implemented using numerous web application frameworks including, for example, PHP, JavaServer, ASP.NET, Cold Fusion, or similar web applications. However, the preceding examples are included for illustrative purposes only, as many other web application frameworks exist and may be used to implement the web applications. Web server 102 may also include other components that are discussed in more detail later in this disclosure, such as a processor, one or more memory components, or one or more network interfaces, for example.

The client devices 108a, 108b, and 108c may be used to help carry out the methods described herein. The client devices may be any sort of computing device, such as a laptop computer, desktop computer, network terminal, mobile computing device (e.g., smart phone), etc. In other illustrative embodiments, the client devices may take the form of a portable media device, personal digital assistant, notebook computer, or any other mobile device capable of accessing web server 102 over the Internet 106.

Data storage 110 may include one or more computer-readable storage media that can be read or accessed by at least one of the client devices 108a, 108b, and 108c or web server 102, for example. The one or more computer-readable storage media may include volatile and/or non-volatile storage components, such as optical, magnetic, organic or other memory or disc storage. In some embodiments, the data storage 110 may be implemented using a single physical device (e.g., one optical, magnetic, organic or other memory or disc storage unit), while in other embodiments, the data storage 110 may be implemented using two or more physical devices. In FIG. 1, data storage 110 is depicted as a "cloud-based" data storage unit (i.e. storage that is off-site with respect to web server 102 or client devices 108a-c). However, data storage 110 may also be implemented on-site with respect to web server 102 or client devices 108a-c.

Figure 2A:
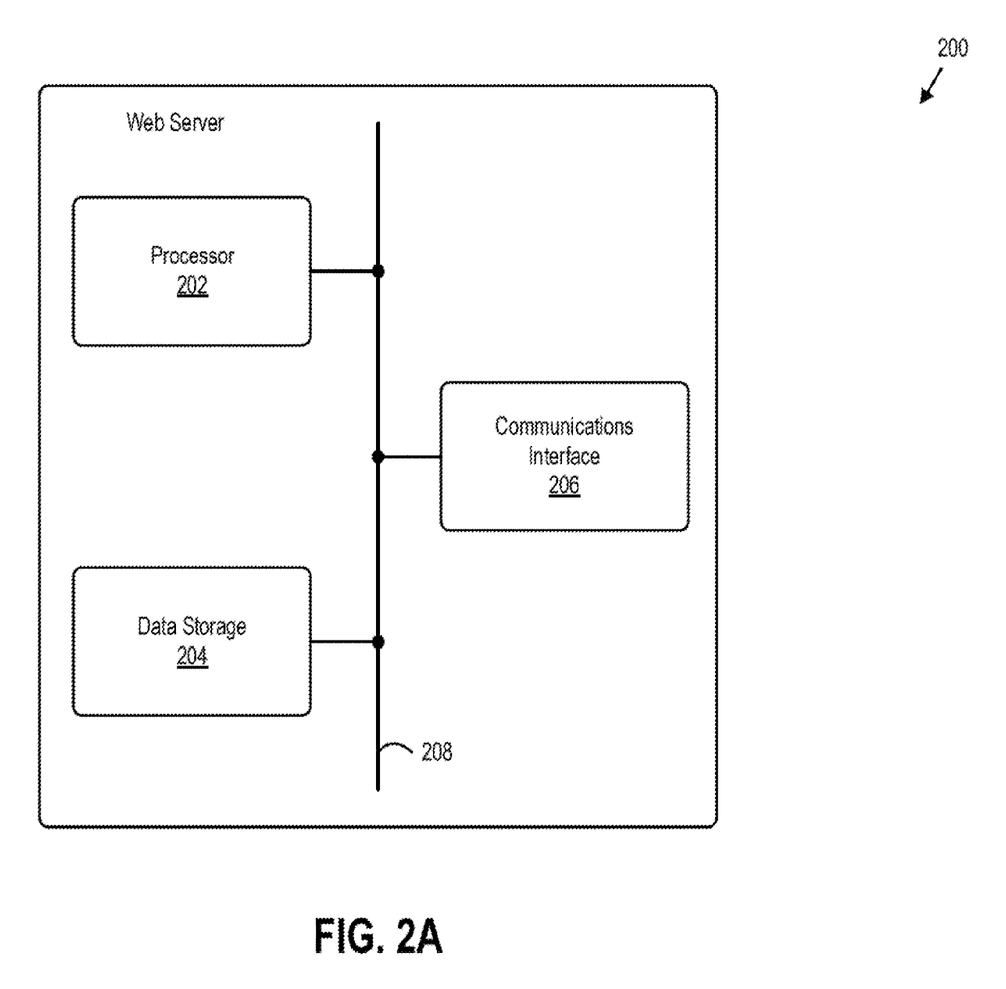
FIG. 2A illustrates a simplified embodiment of an example web server that may be used with the system of FIG. 1.

Data storage 110 may contain data (e.g., patient data sets, correlation data, etc.) capable of being manipulated by a processor, as well as stored program logic executable by the processor. By way of non-limiting example, data in data storage 110 may contain one or more stored datasets that include patient information, information about disease symptoms of the patients, and actions of the patients. In some examples, data storage 110 may also contain data representing recommended actions to be taken by patients and information on correlations determined and tested by the system. Additionally, data storage 110 may also contain stored program logic that is executable by a processor of web server 102 (e.g., shown in FIG. 2) to carry out the various software functions described herein. Data storage 110 may be provided via a SAAS (software as a service) or PAAS (platform as a service) implementation. Some embodiments may use Catalyse API for data storage. Instructions for performing methods disclosed herein may also be stored and accessed via SAAS and/or PAAS implementations. The SAAS and PAAS data storage examples are included for illustrative purposes only, as many other storage arrangements could be implemented without departing from the scope of disclosed systems and methods.

3. Web Server Architecture

FIG. 2A is a simplified block diagram depicting an example web server 200 configured to operate in accordance with various embodiments. Web server 200 may be similar or identical to web server 102 discussed in reference to FIG. 1. Web Server 200 may be a personal computer, laptop computer, or some other type of device that communicates with other communication devices via point-to-point links or via a network, such as Internet 106 shown in FIG. 1. In a basic configuration, web server 200 may include one or more processors 202, data storage 204, and a communication interface 206. A memory bus 208 can be used for communicating among the processor 202, data storage 204, and the communication interface 206.

Processor 202 may include one or more CPUs, such as one or more general purpose processors and/or one or more dedicated processors (e.g., application specific integrated circuits (ASICs) or digital signal processors (DSPs), etc.). Data storage 204, in turn, may comprise volatile and/or non-volatile memory and can be integrated in whole or in part with processor 202. Data storage 204 may hold program instructions executable by processor 202, and data that is manipulated by these instructions, to carry out various functions described herein. Alternatively, the functions can be defined by hardware, firmware, and/or any combination of hardware, firmware, and software.

Communication interface 206 may take the form of a wired or wireless connection, perhaps operating according to IEEE 802.11 or any other protocol or protocols used to communicate with other communication devices or a network. Other forms of physical layer connections and other types of standard or proprietary communication protocols may be used over communication interface 206. Furthermore, communication interface 206 may comprise multiple physical or logical network interfaces, each capable of operating according to the same or different protocols.

In addition to the components and functions discussed above, web server 200 may support additional components and functions, including components and functions used to perform any of the methods described herein.

4. Client Device Architecture

Figure 2B:
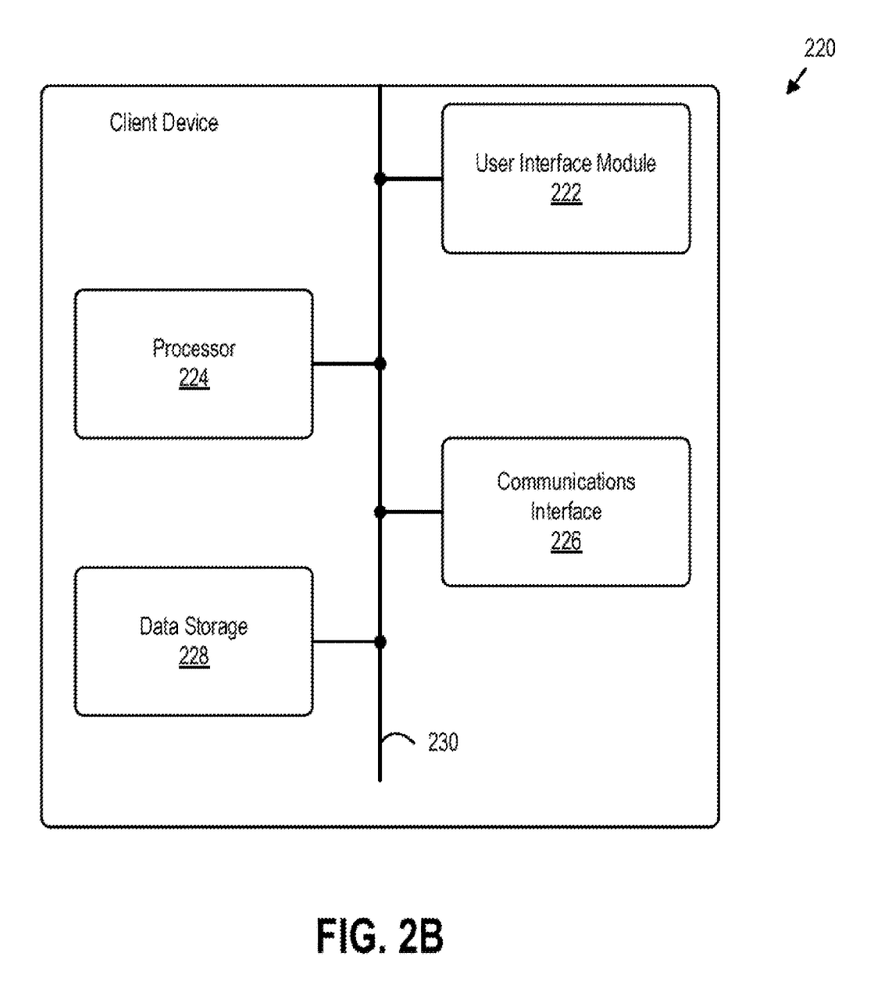
FIG. 2B illustrates a simplified embodiment of an example client device that may be used with the system of FIG. 1.

FIG. 2B is a simplified block diagram depicting an example client device 220 configured to operate in accordance with various embodiments. Client device 220 may be similar or identical to client devices 108a-c, discussed in reference to FIG. 1.

The client device 220 may include a user interface module 222, a communication interface 226, one or more processors 224, and data storage 228, all of which may be linked together via a system bus, network, or other connection mechanism 230. The user interface module 222 may be operable to send data to and/or receive data from external user input/output devices. For example, the user interface module 222 may be configured to send/receive data to/from user input devices such as a keyboard, a keypad, a touch screen, a computer mouse, a track ball, a joystick, and/or other similar devices, now known or later developed. The user interface module 222 may also be configured to provide output to user display devices, such as one or more cathode ray tubes (CRT), liquid crystal displays (LCD), light emitting diodes (LEDs), LED displays, displays using digital light processing (DLP) technology, printers, light bulbs, and/or other similar devices, now known or later developed. The user interface module 222 may also be configured to generate audible output(s), such as via a speaker, speaker jack, audio output port, audio output device, earphones, and/or other similar devices, now known or later developed.

The communications interface module 226 may be configurable to communicate via a network, such as the Internet 106 shown in FIG. 1.

Communication interface 226 may take the form of a wired or wireless connection, perhaps operating according to IEEE 802.11, CDMA, 3G, LTE, 4G, or any other protocol or protocols used to communicate with other communication devices or a network. Other forms of physical layer connections and other types of standard or proprietary communication protocols may be used over communication interface 226. Furthermore, communication interface 226 may comprise multiple physical or logical network interfaces, each capable of operating according to the same or different protocols.

The data storage 228 may include computer-readable program instructions and perhaps additional data. In some embodiments, the storage 228 may additionally include storage required to perform at least part of the herein-described techniques and/or at least part of the functionality of the herein-described devices and systems. For example, data storage 228 may store data corresponding to patient actions, characteristics, and/or symptoms, and it may also store instructions executable to perform statistical analysis of the data or other methods disclosed herein. In such a case, the statistical analysis may be performed by the client device 220.

The one or more processors 224 may include one or more general purpose processors (e.g., microprocessors manufactured by Intel or Advanced Micro Devices) and/or one or more special purpose processors (e.g., digital signal processors, application specific integrated circuits, etc.). The one or more processors 224 may be configured to execute computer-readable program instructions that are contained in the data storage 228 and/or other instructions as described herein. Instructions contained in data storage 228 may be executable by processor 224 so that client device 220 may execute at least part of the methods disclosed herein. The data storage 228 may include one or more computer-readable storage media that can be read or accessed by at least one of the processors 224. The one or more computer-readable storage media may include volatile and/or non-volatile storage components, such as optical, magnetic, organic or other memory or disc storage, which can be integrated in whole or in part with at least one of the processors 224. In some embodiments, the data storage 228 may be implemented using a single physical device (e.g., one optical, magnetic, organic or other memory or disc storage unit), while in other embodiments, the data storage 228 may be implemented using two or more physical devices.

5. Determining Correlations Between Patient Actions and Disease Symptoms

Figure 3A:
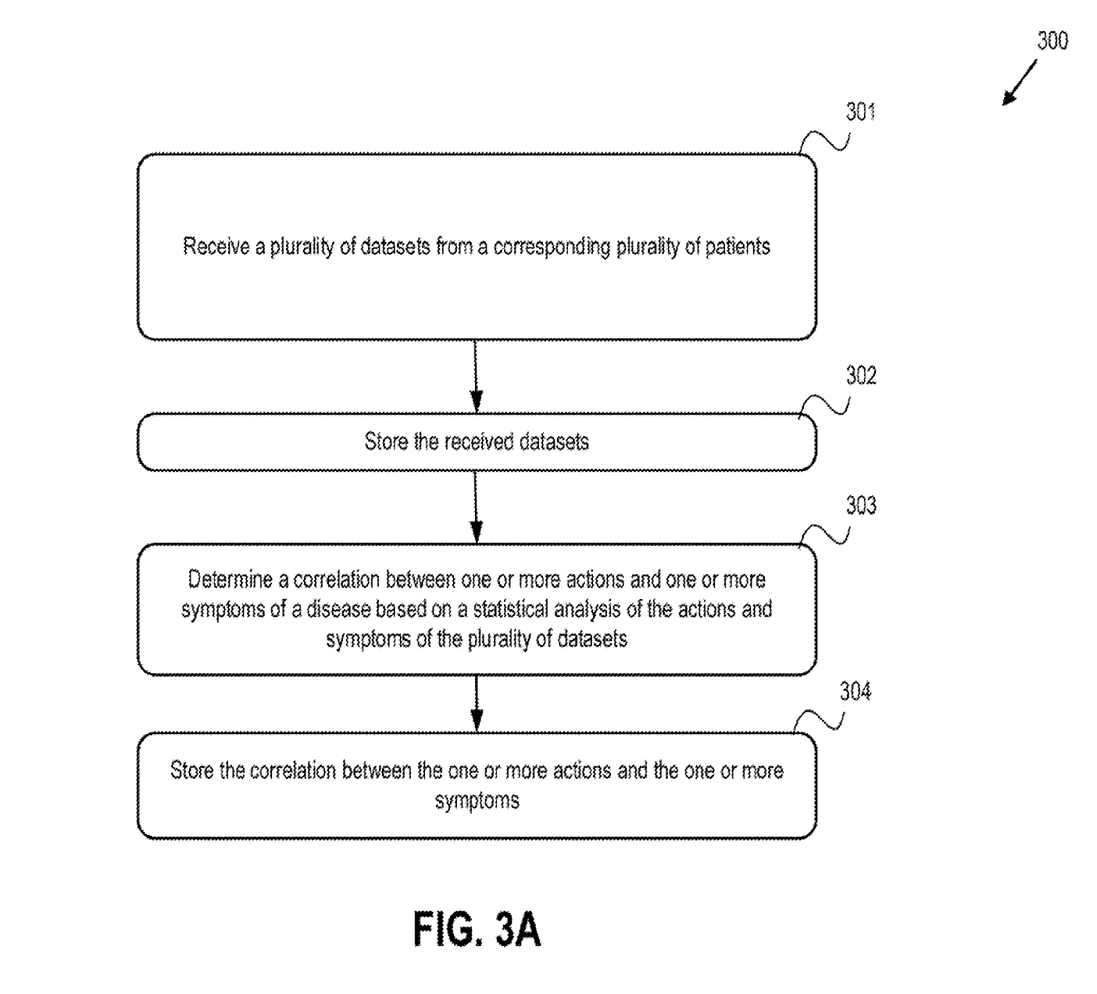
FIG. 3A illustrates a flow chart of one example embodiment for determining a correlation between one or more actions of patients and one or more symptoms of a disease of the patient based on a statistical analysis of the actions and symptoms.

FIG. 3A illustrates a method 300 for creating a predictive model of a medical outcome, according to example embodiments. This method may be carried out, for example, using the network environment 100 described in reference to FIG. 1. Method 300 may include one or more operations, functions, and/or actions as illustrated by one or more of blocks 301-304. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

In addition, for the method 300 and other processes and methods disclosed herein, the flowchart shows functionality and operation of one possible implementation of present embodiments. In this regard, each block may represent a module, a segment, or a portion of program code, which includes one or more instructions executable by a processor or computing device for implementing specific logical functions or steps in the process. The program code may be stored on any type of computer readable medium or memory, for example, such as a storage device including a disk or hard drive or other form of memory media. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device.

First, at step 301, the method includes receiving, at a computing device, a plurality of datasets from a corresponding plurality of patients. In some embodiments, the method may include receiving a single dataset pertaining to one patient or a plurality of datasets pertaining to that one patient. Each patient has at least one corresponding disease, and an individual dataset for an individual patient may include information about at least one disease symptom of the individual patient and at least one action of the individual patient. The computing device may be, for example, any computing device capable of acting as web server 102 and running web applications 104a-c. The datasets may be received from a user (e.g., input by a user or reported by monitoring devices associated with the user (e.g., heart rate monitors, blood glucose monitors, body temperature monitors, personal activity monitors, etc.)), for example. In some instances the user may be the patient, and in others the user may be a person acting on behalf of the patient. In one example, multiple users (e.g., patients) may use the client devices 108a, 108b, and/or 108c to enter in their corresponding dataset. Each user may, for example, utilize a graphical user interface displayed via a web page or a native application on the client device 108a-c to enter their respective dataset. In other examples, the dataset may be received from a server or other network, for example.

The disease of each patient may be any currently known disease, and the disease symptom may be any symptom that corresponds to the disease. In some circumstances the symptom may be a new and previously unknown symptom. The action may be any action that may influence or affect the medical condition of the patient and could be a new and previously unknown action. For example, the action may include consumption of a particular food product, ingestion of a particular therapeutic agent, application of a particular therapeutic agent, ingestion of a particular dietary supplement, performance of a particular physical activity, or exposure to a particular chemical agent. Alternatively, the action may include avoiding or refraining from consuming a particular food product, avoiding or refraining from ingesting a particular therapeutic agent, avoiding or refraining from using a particular therapeutic agent, avoiding or refraining from ingesting a particular dietary supplement, avoiding or refraining from performing a particular physical activity, or avoiding exposure to a particular chemical agent. The action may also include exposure to or avoiding exposure to an environmental factor, such as such as certain weather or temperature conditions like rain, snow, high or low humidity, or high or low temperatures. In some examples, an action may include multiple actions or a quantification of an aspect of an action. For instance, an action may include applying a therapeutic agent according to a particular schedule for a period of time, e.g., three times a day for ten days. Other actions are possible and contemplated herein.

After the datasets are received, the process then proceeds to step 302. At step 302, the received datasets are stored in a database comprising a tangible, non-transitory computer readable media. In some embodiments, the method may include storing a single dataset or a plurality of datasets pertaining to one patient. The computer readable media may include non-transitory computer readable media, for example, such as computer-readable media that stores data for short periods of time like register memory, processor cache and Random Access Memory (RAM). The computer readable media may also include non-transitory media, such as secondary or persistent long term storage, like read only memory (ROM), optical or magnetic disks, compact-disc read only memory (CD-ROM), for example. The computer readable media may also be any other volatile or non-volatile storage systems. In another example, the computer readable-media may take the form of the computer-readable medium as described with reference to FIG. 5.

In preferred embodiments, the computing device receives datasets from a plurality of patients over varying timeframes, e.g., days, weeks, months, or even years. Preferably, the plurality of patients includes a statistically significant number of patients from which to determine correlations between patient actions and disease symptoms (and in some cases, correlations between patient actions, disease symptoms, and patient characteristics). But, in some embodiments, the correlation may be generated for a single patient based on a dataset including only that patient's past actions, disease symptoms and/or characteristics. However, preferably, the plurality of patients is quite large, such as on the order of a few thousand to tens of thousands. However, a smaller plurality of patients could be used with a corresponding reduction in confidence levels corresponding to determined correlations. In operation, an individual dataset corresponding to an individual patient may contain inputs received from that patient over a span of days, weeks, months, or even years. Thus, over time, the database will contain many similar datasets from many different patients having the same disease. Indeed, the database can store datasets from many different patients, e.g., many hundreds, thousands, or even millions of patients.

The database may be a relational database or any other type of database, and may be implemented with data storage that is the same or similar to the data storage 110 discussed with reference to FIG. 1. The database may include other information about each of the patients. For example, the database may include patient characteristics comprising a medical profile for the patient including, for example, the age, sex, height, weight, allergies, ethnicity, medications, medical history, or other characteristics of the patient. The database may also store more or less information regarding the current disease of each patient. For example, the database may include information regarding the severity of the disease or a detailed description of the disease. Other information that is relevant to the medical background of the patient may be included as well.

Once the data has been stored, at step 303, a correlation between one or more actions and one or more disease symptoms may be determined based on a statistical analysis of the actions and symptoms of the plurality of datasets received from the corresponding plurality of patients. In some embodiments, the method may include determining a correlation between one or more actions and one or more symptoms included in a single dataset that pertains to a single patient. To do so, various algorithms and processes may be used. In one embodiment, determining the correlation may include performing a multivariate analysis of, for example, the actions and symptoms stored in the database. The multivariate analysis may be performed using Equations 1 and 2, for example.

5.1 Equation 1

$$X = TP^T \text{ with } TT^T = I$$

5.2 Equation 2

$$Y = TBC^T$$

Equations 1 and 2 allow a fundamental relationship between two matrices, X and Y, to be determined. In Equations 1 and 2, I observations described by K dependent variables are stored in an I×K matrix denoted Y, and the values of J predictors collected on these I observations are collected in the I×J matrix X. In Equations 1 and 2, I represents the identity matrix; T represents the score matrix; and P represents the loading matrix. In Equation 2, B represents a diagonal matrix with regression weights as diagonal elements. Using these equations, Y can be predicted from matrix X.

5.3 Equation 3

$$Y = XB + E$$

Equation 3 is a simplified variant of Equations 1 and 2. Similar to Equations 1 and 2, Equation 3 also allows a fundamental relationship between two matrices, X and Y, to be determined. In Equation 3, similar to Equations 1 and 2, the I observations described by K dependent variables are stored in an I×K matrix denoted Y, and the values of J predictors collected on these I observations are collected in the I×J matrix X. B represents a P by M regression coefficient matrix, and E is a noise term for the model which has the same dimensions as Y. Using this equation, Y can be predicted from matrix X. The final prediction of Y should be the same for this variation of PLSR, but the components differ from those set out in Equations 1 and 2.

Within the context of this disclosure, the observations are meant to be the patients, and the predictors are the actions (and also the characteristics in some instances) of the patients. The predictors may be any of the actions discussed with reference to step 301, for example. The responses, or value of the predictors, are the medical outcomes or symptoms. Accordingly, I=patients, J=actions; and K=medical outcomes or symptoms. In some embodiments, the prediction functionality may be implemented with proprietary or open-source machine learning systems or SaaS services such as BigML.

For example, a researcher may want to predict the subjective evaluation of a headache. The dependent variables that the researcher may like to predict for the headache are the duration and severity of the headache (i.e., disease symptoms). The predictors may be the amount of medicine taken and amount of sleep obtained (i.e., patient actions). Using Equations 1 and 2, or Equation 3, a subset of latent variables or their linear or non-linear combination may be extracted that may explain the duration and/or severity of the headache.

In another example embodiment, determining the correlation between one or more actions and one or more symptoms of a disease based on a statistical analysis of the actions and symptoms of the plurality of datasets received from the corresponding plurality of patients may include modeling a Boolean network of the actions and symptoms previously stored in the database at step 302, for example. In some embodiments, the method may include modeling a Boolean network of the actions and symptoms previously stored in the database from a single dataset or datasets that pertains to a single patient. A Boolean network may include a number of discrete binary variables—such as patient actions, characteristics, or symptoms—that are interrelated via Boolean functions that define dependencies of some variables upon others. In other embodiments, neural networks or other machine learning techniques or predictive algorithms may be used to determine a correlation between patient actions and disease symptoms.

After the correlation has been determined, at step 304, the correlation between the particular action and the at least one symptom may be stored in the database. The correlation may be stored in a manner similar to the datasets discussed above with reference to step 302, for example. In one instance, the correlation is stored in a manner that associates the correlation with the relevant patients.

In preferred embodiments, the correlation is based on a plurality of patient datasets collected from patient data received from a plurality of patients over time. Thus, the correlation determined at step 304 may be based upon an analysis of data aggregated from many hundreds, thousands, or even millions of patient datasets. However, in other embodiments the correlation may be based on a dataset or datasets collected from a limited number of patients (even a single patient in some instances.)

Additionally, correlations between specific patient actions and disease symptoms may be stored in the database. In operation, each correlation may have a confidence factor or similar assessment corresponding to the strength of the correlation between the action and its effect on a disease symptom. For example, if the datasets showed that eating three servings of broccoli a week lowered blood pressure by 30% in 85% of patients with heart disease, then consumption of three servings of broccoli per week would be considered highly correlated with lowering blood pressure. Likewise, if consuming three servings of peanut butter a week lowered blood pressure by 5% in 15% of patients with heart disease, then consumption of that amount of peanut butter would be considered weakly correlated with lowering blood pressure. But if consuming seven servings of peanut butter a week (i.e., once a day) lowered blood pressure by 30% in 50% of patients, then daily consumption of peanut butter would be considered highly correlated with lowering blood pressure. In operation, correlations between actions and disease symptoms can be reassessed as more data is received from patients. In this manner, each determined correlation and the corresponding strength or weakness of correlation can be continually (or least frequently) revised as new data is received from patients.

Figure 3B:
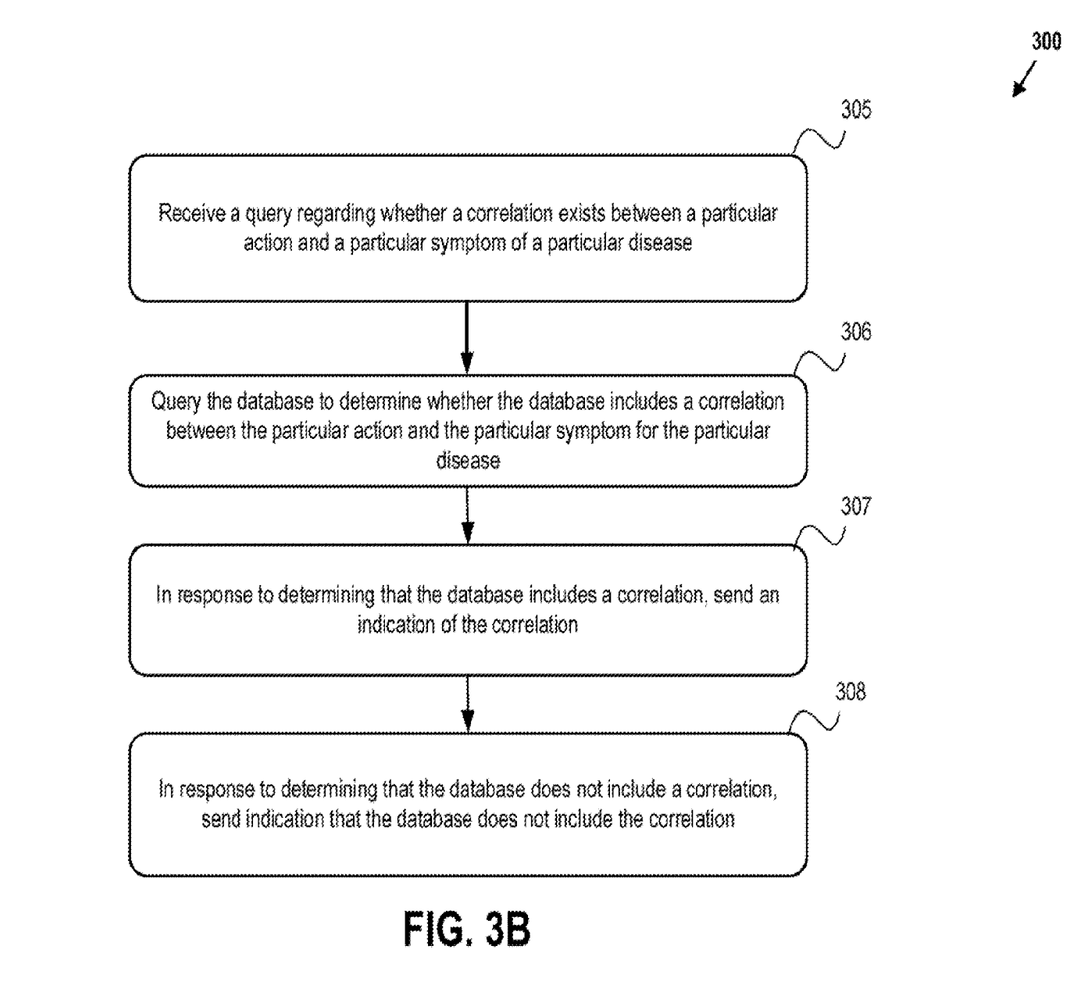
FIG. 3B illustrates a flow chart according to one alternative embodiment for determining a correlation between one or more actions of patients and one or more symptoms of a disease of the patient based on a statistical analysis of the actions and symptoms.

FIG. 3B shows another example embodiment of additional or alternative steps of the method 300 shown in FIG. 3A. In FIG. 3B, the method additionally includes steps 305-308. At step 305, the computing device may receive a query regarding whether a correlation exists between a particular action and a particular disease symptom.

In response to receiving the query, at step 305, the computing device may query the database to determine whether the database includes a correlation between the particular action and the particular symptom for the particular disease. The particular action and particular symptom may be any of the symptoms and actions discussed above with regard to steps 300-304.

In response to determining that the database includes a correlation between the particular action and the particular symptom, the computing device may send an indication of the correlation, and in response to determining that the database does not include a correlation between the particular action and the particular symptom, the computing device may send an indication that the database does not include a correlation between the particular action and the particular symptom. Sending an indication may comprise sending a notification to one of a client device 108a-c of which a patient is using, for example. The notification may comprise any signal or message capable of relaying the information, for example.

In some embodiments, the indication sent by the computing device may correspond to at least one of the following types: (i) sufficient data has been collected and analyzed to conclude that performing the particular action (or refraining from the action) has been correlated with an improvement (or worsening) of the particular disease symptom; (ii) sufficient data has been collected and analyzed to conclude that performing the particular action (or refraining from the action) has not been found to be correlated with an improvement (or worsening) of the particular disease symptom; or (iii) sufficient data has not been collected and analyzed to conclude that performing the particular action (or refraining from the action) has any correlation to an improvement (or worsening) of the particular disease symptom (i.e., insufficient data). As the system collects more data from the plurality of patients over time, the ability of the system to determine correlations and send responsive indications of the first two of the three types should improve.

Figure 3C:
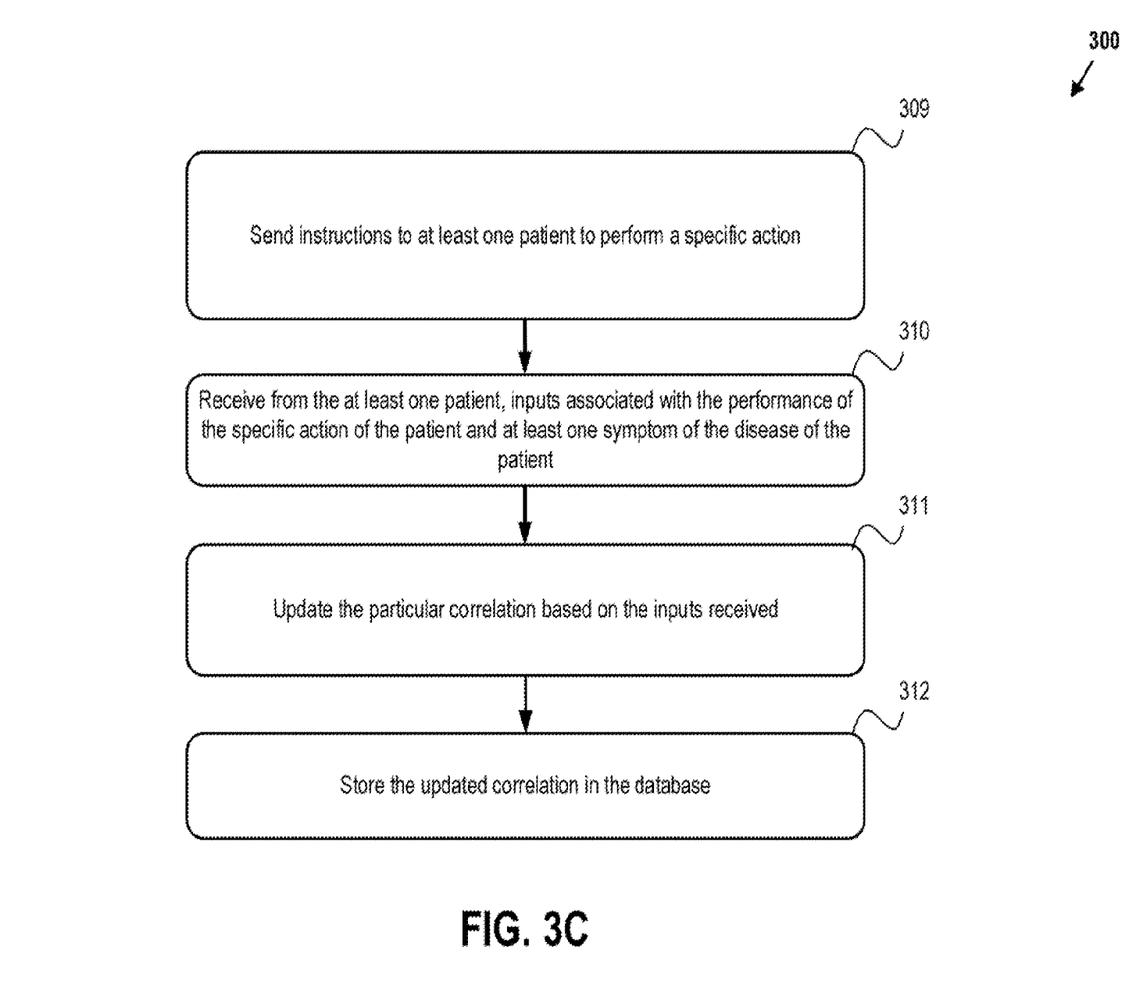
FIG. 3C illustrates a flow chart according to another alternative embodiment of a method for determining a correlation between one or more actions of patients and one or more symptoms of a disease of the patient based on a statistical analysis of the actions and symptoms.

FIG. 3C shows an even further example embodiment of additional or alternative steps of the method shown in FIG. 3A. In FIG. 3C, the method additionally includes steps 309-312. At step 309, the computing device may further be configured to send instructions to at least one patient to perform a specific action. The specific action may be selected to test a particular correlation stored in the database. For example, if a particular correlation is suspected between the particular action and the particular symptom—from an indication returned from steps 305-308 of FIG. 3B, for example—then the computing device may suggest modifications to the particular habits or activities of the particular patient. As the patient engages in the new activity, new data may be obtained from the patient based on that activity, and at step 310, the computing device may be configured to receive from the patient, inputs associated with the performance of the specific actions of the patient and at least one symptom of the disease of the patient. The new data may be obtained from the patient in a manner similar to that explained in reference to step 301, for example.

Once the inputs associated with the performance of the specific action of the patient and at least one symptom of the disease of the patient have been received, the particular correlation based on the inputs received from the at least one patient may be updated, and any updates may be stored in the database. In some embodiments, a new correlation may be made based on the inputs received from the patient. In such an instance, the correlation may be determined, for example, using a multivariate statistical analysis. The multivariate analysis may be performed using the method described with reference to FIG. 3A, for example. In some embodiments, the inputs collected from the patient after the patient has performed certain actions and the corresponding effects on the patient's disease symptoms (if any) may be statistically analyzed separately from other action and symptom inputs collected from the patient. In such embodiments, conducting the statistical analysis of these particular actions and effects separately may improve the likelihood of identifying a correlation between a particular action and any change (improvement or degradation) in disease symptoms.

In operation, if one patient performs an action that improves one of that patient's disease symptoms, then the system may advise other patients to perform that same action to determine whether and the extent to which that action improves the same disease symptom in the other patients, thereby collecting data to verify or disprove a potential correlation. For example, in some embodiments, once the system recognizes a potential correlation between a particular action and a certain disease symptom, the system may instruct additional patients to perform that particular action for the purpose of collecting further data from the additional patients who perform the particular action in response to the instruction.

If the further data collected from the additional patients does not establish a sufficient statistical correlation between the particular action and an improvement in the disease symptom, then the system may conclude that the particular action and the disease condition are not statistically correlated, thus disproving the potential correlation. But if the further data collected from the additional patients corroborates the potential correlation, then the system may instruct even more patients to perform that particular action to obtain sufficient data to determine that a correlation exists between the particular action and the disease symptom. Thus, in this manner, the system tests potential correlations across different patient populations over varying timeframes to either verify or disprove newly-identified potential correlations. And once the system has sufficient statistical information to verify that a potential correlation is an actual correlation, the system may instruct still further patients to perform the particular action and to collect data from the still further patients to improve the reliability (or confidence factor) associated with the verified correlation.

Figure 4:
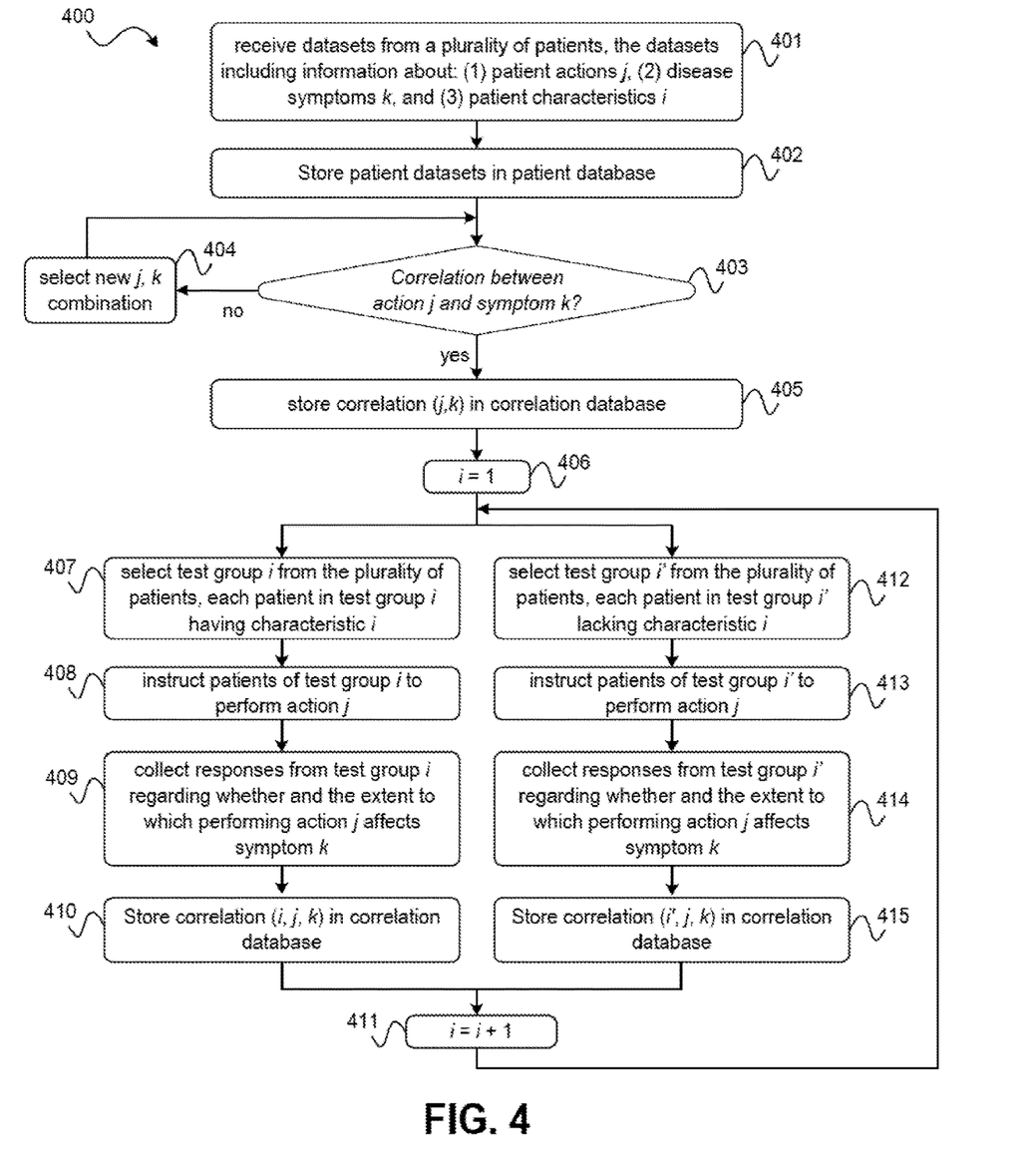
FIG. 4 illustrates a flow chart for an algorithm 400 according to some embodiments for determining a correlation and testing the correlation with a patient population.

FIG. 4 illustrates a flow chart for an algorithm 400 according to some embodiments for (i) determining a correlation between one or more patient actions, a disease symptom, and one or more patient characteristics, and (ii) testing the determined correlations.

Algorithm 400 starts at block 401, where datasets are received from a plurality of patients. The datasets comprise information about (1) a plurality of patient actions; (2) a plurality of disease symptoms; and (3) a plurality of patient characteristics. Next, at block 402, the patient datasets are stored in a patient database. The patient database may be implemented in any type of data storage, including but not limited to data storage 110 shown and described with reference to FIG. 1.

In operation, the datasets from the plurality of patients are received over time. For example, certain patient characteristics may be received when a patient sets up an initial patient medical profile (e.g., sex, birthdate, height, weight, illnesses, allergies, etc.). The system may receive further patient characteristics or keep a running history of certain patient characteristics to supplement/update the patient's medical profile as those characteristics change over time (e.g., weight, blood pressure, blood sugar level, temperature, etc.).

Different patient characteristics may be stored for different diseases and/or disease symptoms because different patient characteristics may be more important for some diseases and/or disease symptoms than for others. For example, blood sugar may be more important for a patient with diabetes but less important for a patient with recurring sinus infections. Additionally, some patient characteristics may be collected with more frequency than others. For example, a patient's blood pressure might be collected daily, a patient's weight might be collected weekly, and a patient's age might be collected only once.

After receiving patient datasets at block 401 and storing the patient datasets in the patient database at block 402, algorithm 400 proceeds to blocks 403 and 404, where algorithm 400 determines whether correlations exist between (1) sets of one or more particular patient actions and (2) any particular disease symptoms stored in the patient database. The detailed historical data collected from a plurality of patients enables the algorithm to look for correlations between disease symptoms and sets of one or more individual actions. For example, if the disease is migraine headaches, and the symptom is nausea, the system can determine whether there is a correlation between (1) migraine-induced nausea and (2) consuming more than 200 mg of caffeine in a day. Similarly, the system can determine whether there is a correlation between, for example, (1) migraine-induced nausea and (2) a combination of (a) getting an average of 8 hours of sleep each night, (b) performing 20 minutes or more of aerobic exercise at least three times a week, and (c) consuming more than 200 milligrams of caffeine in a day. Such a correlation can be determined by using one or more different statistical methods, including but not limited to the statistical methods described herein.

If at block 403, the algorithm 400 determines that the data in the patient database does not show a correlation between a particular patient action j and a particular disease symptom k, algorithm 400 proceeds to block 404 where a new action/symptom set (j,k) is selected. Although block 404 shows an action/symptom set (j,k) as having a single action and a single symptom, some embodiments may use an action/symptom set having more than one action as described above (e.g., an action/symptom set $(j_1, j_2, k)$ or $(j_1, j_2, j_3, k)$).

After selecting a new action/symptom set, the algorithm 400 returns to block 403 to determine whether a correlation exists between the patient action and disease symptom of the new action/symptom set. Because datasets are collected from patients over time, new data may indicate a correlation between a particular action and a particular symptom only after a statistically significant set of data is available for analysis. Therefore, even though the statistical analysis performed at block 403 may not initially indicate a correlation between the action and symptom of a particular action/symptom set, the algorithm 400 is configured to periodically reconsider whether a correlation exists either on a regular schedule or perhaps in response to a query as described elsewhere herein.

If the algorithm 400 determines at block 403 that the data in the patient database shows a correlation between a particular patient action j and a particular disease symptom k, the algorithm 400 proceeds to block 405 where the determined correlation is stored in a correlation database. The correlation database may be implemented in any type of data storage, including but not limited to data storage 110 shown and described with reference to FIG. 1.

After storing the determined correlation in the correlation database at block 405, the algorithm 400 proceeds to block 406, where the algorithm begins the process of verifying whether and the extent to which the determined correlation (action j, symptom k) exists in different patient groups.

In preferred embodiments, patients are organized into test groups based on at least one shared patient characteristic, i. For example, a patient characteristic may correspond to the sex, age (or age range), height, weight, ratio of height to weight, ethnicity, allergy, frequency of disease symptom, manifestation of disease symptom, etc. In some embodiments, patients may be organized into test groups based on a multiple shared patient characteristics. For example, a test group may include men of a particular ethnicity within a certain age range and having a particular type of disease symptom manifestation. However, even in such embodiments, all of the patients in the test group will share at least one common patient characteristic.

In operation, the patients for the test group may be selected in many different ways. For example, in some embodiments, the patients for a particular test group may be selected and grouped by the system based on information in the patient database. In other embodiments, the system may solicit patients having certain patient characteristics to join a test group. In still further embodiments, the system may respond to solicitations from patients to join a particular test group. In yet still further embodiments, patients may be selected for a particular test group based on any combination of the aforementioned methodologies.

In the example shown in FIG. 4, the algorithm 400 selects patients for patient group i, where each patient in patient group i has at least patient characteristic i in common After selecting a set of patients for test group i at block 407, the algorithm 400 proceeds to block 408, where patients in test group i are instructed to perform action j of the determined correlation (action j, symptom k). Preferably, some of the patients in test group i are instructed to refrain from performing action j for some defined period of time (e.g., two weeks, four weeks, etc.) to baseline the patients in test group i.

Then, at block 409, responses from the patients in test group i are collected. The responses preferably include information on whether and the extent to which performing action j had an effect on each patient's disease symptom k.

After collecting responses from the patients in test group i at block 409, algorithm 400 then proceeds to block 410 where the correlation (positive or negative) between action j, symptom k, and patient characteristic i is stored in the correlation database. A positive correlation means that action j had a positive effect (improved) on disease symptom k for patients having characteristic i. Likewise, a negative correlation means that action j had a negative effect (worsened) on disease symptom k for patients having characteristic i. By storing the correlation (positive or negative) between action j, symptom k, and characteristic i, the system is better able to predict, for a new patient having characteristic i, whether performing action j will improve or worsen disease symptom k.

In some embodiments, the algorithm may use the response data to assign a confidence factor to the positive or negative correlation between action j, symptom k, and characteristic i. In such embodiments, if a particular correlation has a sufficiently high confidence factor (e.g., a confidence factor that exceeds a predetermined confidence factor threshold), the system may test the correlation on other test groups comprising patients having at least patient characteristic i. In this manner, the system can test the importance of patient characteristic i to the correlation between action j and symptom k.

Some embodiments may additionally include blocks 412-415 for further improving the confidence factor associated with the correlation between patient characteristic i, action j, and symptom k. At step 412, a test group i' is selected from the plurality of patients. Each patient in test group i' lacks characteristic i. The patients for test group i' may be selected by any of the selection methodologies described for test group i (i.e., selected based on the information in the patient database, soliciting patients lacking characteristic i, and/or in response to solicitations from patients to join test group i'.)

After selecting patients for test group i' at block 412, algorithm 400 proceeds to block 413, where patients in test group i' are instructed to perform action j of the determined correlation (action j, symptom k). Preferably, some of the patients in test group i' are instructed to refrain from performing action j for some defined period of time (e.g., two weeks, four weeks, etc.) to baseline the patients in test group i'.

Then, at block 414, responses from the patients in test group i' are collected. The responses preferably include information on whether and the extent to which performing action j had an effect on each patient's disease symptom k.

After collecting responses from the patients in test group i' at block 414, algorithm 400 then proceeds to block 415 where the correlation (positive or negative) between action j, symptom k, and patient characteristic i' is stored in the correlation database. A positive correlation means that action j had a positive effect (improved) on disease symptom k for patients lacking characteristic i. Likewise, a negative correlation means that action j had a negative effect (worsened) on disease symptom k for patients lacking characteristic i. By storing the correlation (positive or negative) between action j, symptom k, and the lack of characteristic i, the system is better able to predict the likelihood that characteristic i is a factor in whether performing action j improves or worsens symptom k.

By determining and testing correlations in selected patient test groups according to the method of FIG. 4, the system encourages patients to supply action and symptom data (j, k) that will be most useful in confirming or disproving determined correlations between particular actions and disease symptoms across many different patient groups having varied patient characteristics.

Figure 5:
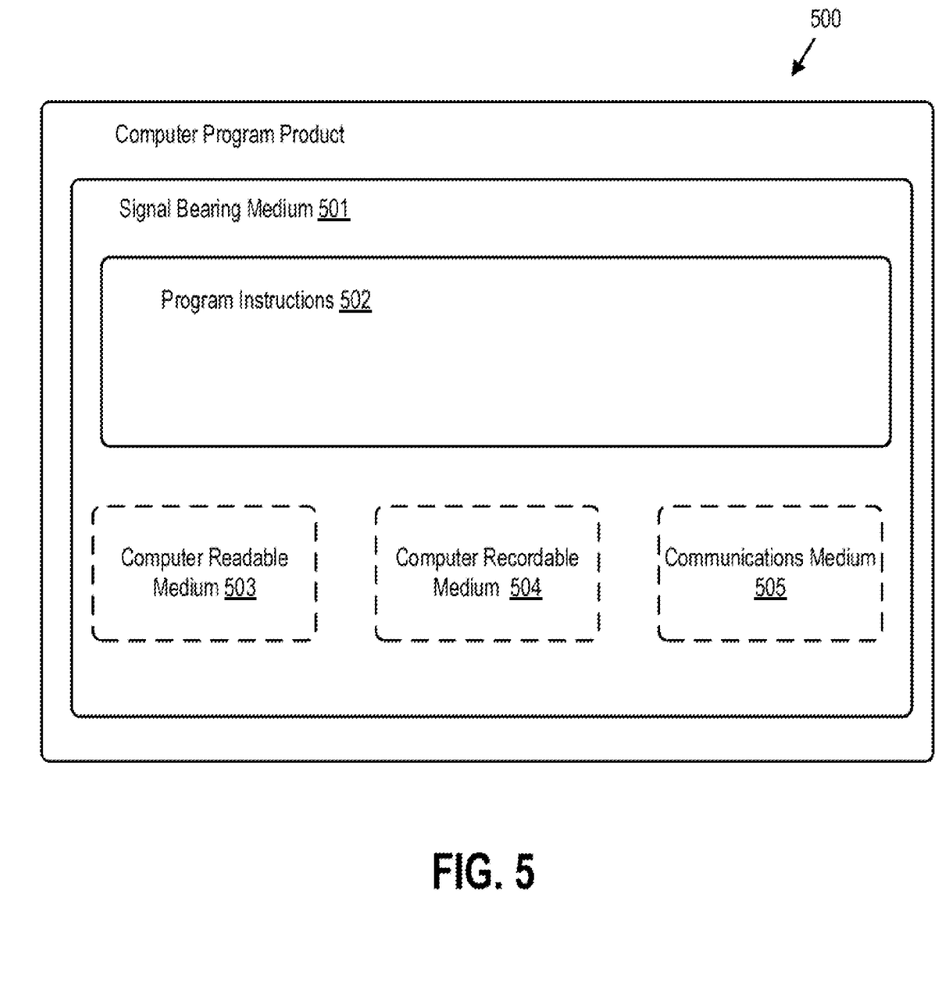
FIG. 5 illustrates an example computer program product according to one embodiment.

In some embodiments, the disclosed methods may be implemented as computer program instructions encoded on a non-transitory computer-readable storage media in a machine-readable format, or on other non-transitory media or articles of manufacture. FIG. 5 shows a schematic illustrating a conceptual partial view of an example computer program product that includes a computer program for executing a computer process on a computing device, arranged according to at least some embodiments presented herein.

In one embodiment, the example computer program product 500 is provided using a signal bearing medium 501. The signal bearing medium 501 may include one or more programming instructions 502 that, when executed by one or more processors may provide functionality or portions of the functionality described above with respect to FIGS. 1-4. In some examples, the signal bearing medium 501 may encompass a computer-readable medium 503, such as, but not limited to, a hard disk drive, a Compact Disc (CD), a Digital Video Disk (DVD), a digital tape, or other forms of computer-based memory, etc. In some implementations, the signal bearing medium 501 may encompass a computer recordable medium 504, such as, but not limited to, memory, read/write (R/W) CDs, R/W DVDs, etc. In some implementations, the signal bearing medium 501 may encompass a communications medium 505, such as, but not limited to, a digital and/or an analog communication medium (e.g., a fiber optic cable, a waveguide, a wired communications link, a wireless communication link, etc.). Thus, for example, the signal bearing medium 501 may be conveyed by a wireless form of the communications medium 505 (e.g., a wireless communications medium conforming with the IEEE 802.11 standard or other transmission protocol).

The one or more programming instructions 502 may be, for example, computer executable and/or logic implemented instructions. In some examples, a computing device such as the web server 102 or a client device 108a-c of FIG. 1 may be configured to provide various operations, functions, or actions in response to the programming instructions conveyed to the computing device by one or more of computer readable medium 503, the computer recordable medium 504, and/or the communications medium 505.

While particular aspects and embodiments are disclosed herein, other aspects and embodiments will be apparent to those skilled in the art in light of the foregoing teaching. The various aspects and embodiments disclosed herein are for illustration purposes only and are not intended to be limiting, with the true scope and spirit being indicated by the following claims.

What is claimed is:

1. A method comprising:
receiving, at a computing device via a graphical user interface, a dataset from a user, wherein the dataset comprises information about at least one disease symptom of the user and at least one particular action of the user;
storing the dataset in a database comprising a tangible, non-transitory computer readable media;
receiving a plurality of datasets from a corresponding plurality of users, each user having at least one corresponding disease symptom, wherein an individual dataset for an individual user includes information about at least one disease symptom of the individual user and at least one action of the individual user;
storing the received plurality of datasets in the database;
determining a threshold amount of data for determining a predicted effect of the particular action on one or more disease symptoms for the user;
in response to reaching the threshold amount of data for determining the predicted effect of the particular action, displaying at the graphical user interface an indication to the user, wherein the indication comprises a recommendation to the user regarding the particular action based on the determined predicted effect between the particular action and the one or more disease symptoms of the user;
in response to not reaching the threshold amount of data for determining the predicted effect of the particular action, displaying at the graphical user interface a prompt, wherein the prompt comprises an instruction to the user to enter more data over time;
based on the user receiving the prompt, collecting a response from the user via the graphical user interface, wherein the response comprises information about at least one disease symptom of the user and at least one action of the user;
determining, by a machine learning system, a correlation between one or more actions and one or more disease symptoms, wherein determining the correlation comprises using a machine learning technique to model the actions and disease symptoms in the plurality of datasets received from the corresponding plurality of users;
storing in the database the correlation between the one or more actions and the one or more disease symptoms determined from the plurality of datasets; and
providing a recommendation to the user based on the determined correlation between the one or more actions and the one or more disease symptoms.

2. The method of claim 1, wherein the at least one action includes at least one of (i) consuming or refraining from consuming a food product, (ii) ingesting or refraining from ingesting a therapeutic agent, (iii) applying or refraining from applying a therapeutic agent, (iv) ingesting or refraining from ingesting a dietary supplement, (iv) performing or refraining from performing a physical activity, (v) exposure to or avoiding exposure to a chemical agent, or (vi) exposure to or avoiding exposure to an environmental factor.

3. The method of claim 2, wherein the at least one action further includes a quantification of at least one aspect of the at least one action.

4. The method of claim 1, wherein the database includes a medical profile for the user comprising one or more of an age, a sex, a height, a weight, and a medical history of the user.

5. The method of claim 1, further comprising:
receiving a query regarding whether a correlation exists between a particular action and a particular disease symptom; and
in response to receiving the query, querying the database to determine whether the database includes the correlation between the particular action and the particular disease symptom; and sending an indication of whether the database includes the correlation between the particular action and the particular disease symptom.

6. The method of claim 1, further comprising:
sending instructions to the user to perform a specific action, wherein the specific action is selected to test a particular correlation stored in the database;
receiving, from the user, inputs associated with the performance of the specific action of the user and at least one disease symptom of the user;
updating the particular correlation based on the inputs received from the user; and
storing the particular correlation in the database.

7. A system comprising:
one or more processors configured to:
(1) receive, via a graphical user interface, a dataset from a user, wherein the dataset includes information about at least one disease symptom of the user and at least one particular action of the user;
(2) store the dataset in a database comprising a tangible, non-transitory computer readable media;
(3) receive a plurality of datasets from a corresponding plurality of users, each user having at least one corresponding disease, wherein an individual dataset for an individual user includes information about at least one disease symptom of the individual user and at least one action of the individual user;
(4) store the received datasets in the database;
(5) determine a threshold amount of data for determining a predicted effect of the particular action on one or more disease symptoms for the user;
(6) in response to reaching the threshold amount of data to determine the predicted effect of the particular action, display at the graphical user interface an indication to the user, wherein the indication comprises a recommendation to the user regarding the particular action based on the determined predicted effect between the particular action and the one or more disease symptoms of the user;

(7) in response to not reaching the threshold amount of data for determining the predicted effect of the particular action, display at the graphical user interface a prompt, wherein the prompt comprises an instruction to the user to enter more data over time;

(8) based on the user receiving the prompt, collect a response from the user via the graphical user interface, wherein the response comprises information about at least one disease symptom of the user and at least one action of the user;

(9) determine, by a machine learning system, a correlation between one or more actions and one or more disease symptoms, wherein determining the correlation comprises using a machine learning technique to model the actions and disease symptoms in the plurality of datasets received from the corresponding plurality of users;

(10) store in the database the correlation between the one or more actions and the one or more disease symptoms determined from the plurality of datasets; and (11) provide a recommendation to the user based on the determined correlation between the one or more actions and the one or more disease symptoms.

8. The system of claim 7, wherein the one or more processors are further configured to determine a correlation between one or more actions and one or more disease symptoms based on a statistical analysis of the actions and disease symptoms in the dataset by performing a multivariate analysis of the actions and disease symptoms stored in the database.

9. The system of claim 7, wherein the one or more processors are configured to determine a correlation between one or more actions and one or more disease symptoms based on a statistical analysis of the actions and disease symptoms in the dataset by modeling a Boolean network of the actions and symptoms stored in the database.

10. The system of claim 7, wherein the one or more processors are further configured to:

(1) receive a query regarding whether a correlation exists between the particular action and a particular disease symptom;

(2) in response to receiving the query, query the database to determine whether the database includes the correlation between the particular action and the particular disease symptom;

(3) in response to determining that the database includes the correlation between the particular action and the particular disease symptom, send an indication of the correlation; and (4) in response to determining that the database does not include the correlation between the particular action and the particular disease symptom, send an indication that the database does not include the correlation between the particular action and the particular disease symptom.

11. The system of claim 7, wherein the one or more processors are further configured to:

(1) initiate transmission of instructions to a user to perform a specific action, wherein the specific action is selected to test a particular correlation stored in the database;

(2) receive, from the user, inputs associated with the performance of the specific action and at least one disease symptom of the user;

(3) update the particular correlation based on the inputs received from the user; and (4) store the updated correlation in the database.

12. The system of claim 11, wherein the one or more processors are configured to update the particular correlation based on the inputs received from the user by:

(1) updating the database to include the inputs received from the user; and (2) performing at least one of (a) a multivariate analysis of the actions and disease symptoms stored in the updated database or (b) a multivariate analysis of the inputs associated with the performance of the specific action of the user and at least one disease symptom of the user.

13. The method of claim 1, wherein the recommendation comprises at least one of (i) a recommendation to avoid taking the particular action based on the particular action being associated with one or more worsened disease symptoms for the user, and (ii) a recommendation to undergo taking the particular action based on the particular action being associated with one or more improved disease symptoms for the user.

14. The method of claim 1, wherein determining the correlation between one or more actions and one or more disease symptoms comprises:

receiving the plurality of datasets from the corresponding plurality of patients, each patient having at least one corresponding disease in common and one or more corresponding patient characteristic in common, wherein the individual dataset for an individual patient includes information about (i) one or more disease symptoms of the individual patient, (ii) one or more patient actions performed by the individual patient, and (iii) one or more characteristics of the individual patient;

storing the plurality of datasets in a patient database;

displaying, via the graphical user interface, an instruction to the patients to perform at least one action;

receiving, via the graphical user interface, information comprising an extent to which performing the at least one action affects one or more disease symptoms;

determining a first correlation between the at least one action and the one or more disease symptoms; and storing the first correlation in a correlation database.

* * * * *